US00PP10441P

United States Patent [19]

Bloom

[11] Patent Number: Plant 10,441

[45] Date of Patent: Jun. 9, 1998

[54] HEUCHERA PLANT NAMED ROSEMARY BLOOM

[75] Inventor: Alan H. V. Bloom, Norfolk, England

[73] Assignee: Blooms of Bressingham, Ltd., Norfolk, England

[21] Appl. No.: 794,060

[22] Filed: Feb. 4, 1997

[51] Int. Cl.[6] ..... A01H 5/00

[52] U.S. Cl. ..... Plt./68.1

[58] Field of Search ..... Plt./68.1

*Primary Examiner*—James R. Feyrer
*Assistant Examiner*—Melissa L. Kimball
*Attorney, Agent, or Firm*—Foley & Lardner

[57] ABSTRACT

A new and distinct cultivar of Heuchera plant named 'Rosemary Bloom', characterized by its large bright coral pink, bell shaped flowers which flower from mid-June into late August, clump-forming low-growing habit with bright green foliage, erect stems which carry flowers in spray form, and its adaptability to cut flower production as well as being an excellent cultivar for border or container use.

1 Drawing Sheet

The present invention relates to a new and distinct cultivar of hardy perennial herbaceous plant of the genus Heuchera, known by the cultivar name 'Rosemary Bloom'. The genus Heuchera is a member of the Saxifragaceae family.

The new cultivar originated from a planned cross hybridization between two selected breeding lines carried out by the inventor Alan H. V. Bloom in a controlled breeding program in Bressingham, Diss, Norfolk, England. The cross was between presently unknown cultivars of *Heuchera brizoides* and *Heuchera sanguinea*. The new cultivar was selected by the inventor as one flowering plant among other seedlings produced by the stated cross.

The first asexual reproduction of 'Rosemary Bloom' was accomplished when vegetative cuttings were taken by the inventor in Bressingham, England in 1987. This and subsequent asexual reproduction by division, basal cuttings and tissue culture have shown that the unique combination of characteristics as herein disclosed for 'Rosemary Bloom' are fixed and retained through successive generations of asexual reproduction.

'Rosemary Bloom' has not been observed under all possible environmental conditions. The phenotype may vary with variations in environment such as temperature, light intensity without, however, any variance in the genotype.

The following observations and measurement describe plants grown in Bressingham, England under normal commercial practice.

The following traits have been repeatedly observed and are determined to be basic characteristics of the new cultivar, which in combination distinguish the new cultivar from others:

1. The flowers have a classic coral bell shape.
2. Large bright coral pink flowers with prominent yellow stamens.
3. The flowers are formed in flower sprays carried on erect wiry stems, with the sprays making excellent cut flowers.
4. Clump-forming, low-growing habit also makes cultivar ideal for use in borders or containers, and provides pleasing backdrop to erect stems and flowers.
5. Bright green foliage veined with a tint of bronzed coppery brown.
6. The plant flowers for many weeks in the Bressingham, England environment, starting in mid-June and continuing through late August.
7. The plant displays excellent vigor and hardiness.
8. The plant thrives best in full sun but will tolerate part shade in well-drained fertile soil that is not allowed to become too dry.

The new cultivar is primarily distinguished from other hybrids of this parentage by flower color, the clump-forming foliage which forms neat hummocks, and by the throat or tube of the flower which is more prominent than on other hybrid cultivars of this type.

The accompanying color photograph comprises a perspective view of the new cultivar growing in a border setting.

The following is a detailed description of the new cultivar, based on plants grown in Bressingham, England. All color determinations are based on The Royal Horticultural Society Colour Chart.

Plant origin: Seedling selection.

Parentage: A cross between *Heuchera brizoides* and *Heuchera sanguinea*.

Habit: Clump forming.

Size: Mature plants are approximately 60 cm in height with a spread of 60 cm.

Root system: Fibrous but woody.

Plant vigor: The new perennial shows vigorous and healthy growth throughout Great Britain.

Blooming habit: Large bright coral pink, coral-bell shaped flowers, borne on erect panicle stems arising from the base of the plant. Stamens are prominent.

Blooming period: From June continuing into late August.

Hardiness: Winter hardy throughout the British Isles. The plant has not been fully tested for maximum summer temperature tolerance above 32°C. (90°F.).

Flowers:

*Petal count.*—Five of equal size.

*Petal shape.*—Campanulate, consisting of a bell shaped cup.

*Flower type.*—Panicle.

*Flower size.*—8–12 mm diameter.

*Carpels.*—2 celled.

*Stamens.*—Yellow in color, 1B.

*Color.*—The petals of mature flowers are 39B in color.

Foliage:

*Shape.*—Broadly ovate, and shallow lobed.

*Type.*—Evergreen perennial.

*Texture.*—Glabrous on upper surface, canescent on lower surface.

*Veins.*—Glandular-pulverulent on upper surface.

*Length.*—16 cm.

*Width.*—6 cm.

*Petiole length.*—1.5 cm.

*Margins.*—Dentate.

*Apex.*—Obtuse.

*Base.*—Cordate.

*Color.*—Mature leaves, early spring to late summer: margins 59A, upper surface 132B, under surface 191B, veins 191A. Mature leaves, early autumn to late winter: upper surface 59A, under surface 191C, veins 191B.

It is claimed:

1. A new and distinct cultivar of Heuchera plant named 'Rosemary Bloom', as illustrated and described.

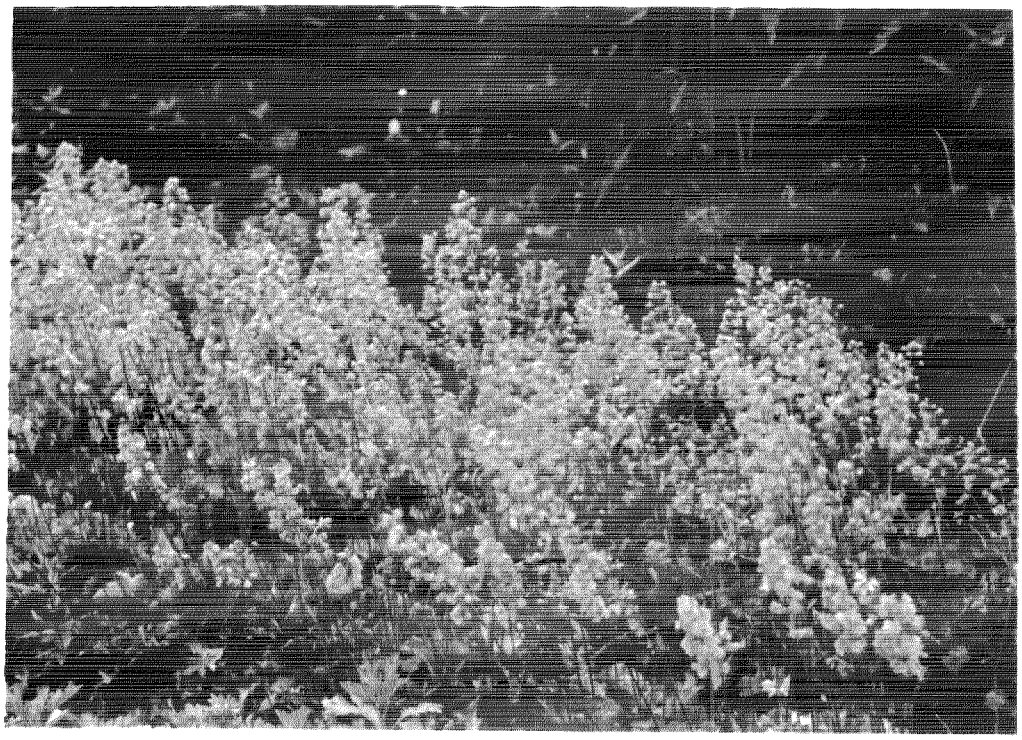

* * * * *